United States Patent [19]

Gordon et al.

[11] 4,017,501
[45] Apr. 12, 1977

[54] PROCESS FOR PREPARING PYRIDINIUM CHLORIDE SALTS OF ALKYL ESTERS OF 2-CHLORO-N-2-HYDROXYETHYLACETAMIDE

[75] Inventors: John Edson Gordon, Martinsville; Robert A. Ralston, Lebanon, both of N.J.

[73] Assignee: American Cyanamid Company, Stamford, Conn.

[22] Filed: Oct. 24, 1975

[21] Appl. No.: 625,407

[52] U.S. Cl. ............................................ 260/295 Q
[51] Int. Cl.² .................................... C07D 213/20
[58] Field of Search ............. 260/295 AM, 295 AM

[56] References Cited

UNITED STATES PATENTS

| | | | |
|---|---|---|---|
| 2,176,896 | 10/1939 | Epstein et al. | 260/295 AM |
| 2,189,664 | 2/1940 | Katzman | 260/295 AM |
| 2,290,173 | 7/1942 | Epstein et al. | 260/295 AM |

OTHER PUBLICATIONS

Kittila, Dimethylformamide Chemical Uses, (1967), pp. 124–126.

Primary Examiner—Norman A. Drezin
Attorney, Agent, or Firm—John L. Sullivan

[57] ABSTRACT

A process for preparing pyridinium chloride salts of esters of 2-chloro-N-2-hydroxyethylacetamide in which no intermediates need be isolated is disclosed.

9 Claims, No Drawings

PROCESS FOR PREPARING PYRIDINIUM CHLORIDE SALTS OF ALKYL ESTERS OF 2-CHLORO-N-2-HYDROXYETHYLACETAMIDE

BACKGROUND OF THE INVENTION

This invention relates to an improved process for the preparation of pyridinium chloride salts of higher aliphatic esters of 2-chloro-N-2-hydroxyethylacetamide.

Epstein et al., in Examples H and I of U.S. Pat. No. 2,290,173, have disclosed the preparation of the lauric acid ester of 2-chloro-N-2-hydroxyethylacetamide. Briefly stated, this preparation involves reacting a lauroyl halide (I) with a 2-chloro-N-2-hydroxyethylacetamide (II) to form an intermediate ester (III) and a hydrogen halide gas. The intermediate ester is isolated, purified and subsequently quaternized with pyridine at 90° to 95° to form a solid mass of the pyridinium halide salt (IV) (1-{{[2-(alkyloyloxy) ethyl] carbamoyl} methyl} pyridinium chloride) which is separated, slurried in benzene, filtered and washed with ligroin to effect purification. This process is outlined in Flow-sheet I.

FLOW SHEET I

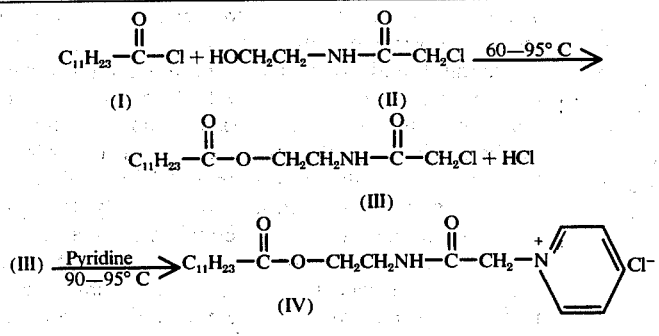

The process of Epstein, however, suffers from three important disadvantages. First, the formation of the intermediate ester (III) is accompanied by the release of irritating, corrosive fumes of hydrogen halide gas. Second, the intermediate ester (III) must be isolated before the final pyridinium chloride can be produced. Finally, the formation of the pyridinium chloride salt (IV) by heating intermediate (III), in pyridine, causes the pyridinium chloride product to be contaminated with pyridine hydrochloride which coprecipitates and must be subsequently removed by repeated slurrying in benzene. Even with the repeated slurrying in benzene, however, the product produced by the process of Epstein is significantly contaminated with pyridine hydrochloride.

Since the pyridinium chloride salts of the higher alkyl esters of 2-chloro-N-2-hydroxyethylacetamide are commercially useful bacteriostatic materials, it would be highly desirable to have a process for their preparation which avoids the difficulties of the Epstein et al., process.

It is an object of the present invention to provide a simplified process, in which no intermediates need be isolated, for the production of the pyridinium chloride salts of the higher alkyl esters of 2-chloro-N-2-hydroxyethylacetamide. It is a further object of this invention to provide a process in which no irritating hydrogen halide fumes are released and in which the pyridinium salt produced contains less pyridinium hydrochloride contaminants than that found in the products produced by the processes in current use.

According to the present invention, it has been discovered that pyridine combined with a non-hydroxylic solvent, that is, a solvent essentially free of water or reactive hydrogen atoms, constitutes a suitable reaction medium for the production of the desired pyridinium chloride salt (IV), from 2-chloro-N-2-hydroxyethylacetamide.

In order to convert the 2-chloro-N-2-hydroxyethylacetamide into the desired pyridinium salt (IV), the hydroxyl group must be esterified, and the halo group must be displaced by pyridine. Although it is possible to conduct these reactions in either order, it is preferable to perform the esterification first, and the quaternization reaction second. Thus, in the preferred reaction sequence, an aliphatic acid halide (I) is reacted with 2-chloro-N-2-hydroxyethylacetamide (II) in a non-hydroxylic solvent, in the presence of pyridine, to form the intermediate ester (III) which is converted in situ to the pyridinium chloride salt (IV). Whether the reaction steps are performed in the preferred order or not, however, the process of the present invention is superior to the Epstein process because all reactions may be carried out in a single reaction vessel without isolation of intermediates; hydrogen halide gas released during the esterification step is absorbed by the pyridine present, and the pyridinium chloride product (IV) is obtained in solution rather than as a solid mass from which it is difficult to isolate. In addition, not only is the product produced by process of the present invention lighter in color, but it also contains less pyridine hydrohalide impurities than the products produced by the prior art method. Because of the lower pyridine hydrohalide levels contained in the product produced by the process of the present invention, a 1% aqueous dispersion of such a product has a pH of 4 to 5.2 at 25° C., while a similar preparation of the prior art product has a pH of 2.5 to 3.8.

Any higher aliphatic acid halide containing from 12 to 18 carbon atoms may be used singly or in mixtures in the process of the present invention. This includes, for example, straight chain acid halides such as lauroyl, myristoyl, palmitoyl and stearoyl bromides or chlorides, and substituted acid halides containing alkoxyl and carboalkoxy groups such as 2-methoxy-dodecanoyl chloride, 4-ethoxy-tetradeconyl bromide, 5-carbohexoxypentanoyl chloride, 9-carbobutoxynonoyl chloride, 7-carbobutoxy heptanoyl chloride and other similar acid halides. The preferred acid halides are lauroyl chloride and a commerical grade of stearoyl chloride which contains predominantly stearoyl chloride, but in addition, some other long chain carboxylic acids chlorides so that the apparent molecular weight of this material is 285.8 rather than 302.9 which would be expected for pure stearoyl chloride.

Non-hydroxylic solvents suitable for use in the present process include ethers such as ethylene glycol dimethyl ether, ethylene glycol diethyl ether, diethylene glycol dimethyl ether, diethylene glycol diethyl ether, triethylene glycol dimethylether, triethylene glycol diethyl ether, tetraethylene glycol dimethyl ether, di-n-butyl ether and tetraethylene glycol diethyl ether; ketones such as ethyl methyl ketone, isopropyl methyl ketone, n-propyl methyl ketone, diethyl ketone, isobutyl methyl ketone, diisopropyl ketone, n-butyl methyl ketone, cyclopentonone, di-n-propyl ketone, cyclohexanone, the methyl cyclohexanones, diisobutyl ketone, and hexyl methyl ketone; aromatic materials such as toluene, zylene, chlorobenzene, nitrobenzene, dichlorobenzene, the chlorotoluenes, bromobenzene and anisole; and aprotic solvents such as dimethyl formamide and sulfolane. It is desirable to add between about 2 and 2.20 moles of pyridine to the nonhydroxylic solvent for each mole of 2-chloro-N-2-hydroxyethylacetamide used in the reaction. If the esterification reaction is performed first, then approximately equimolar quantities of the acid halide and the 2-chloro-N-2-hydroxyethylacetamide are added to the non-hydroxylic pyridine solvent mixture. The reaction mixture is stirred at a temperature from about 10° to 65° C. for a period of about 1 to 4 hours. It is preferred, however, to conduct this reaction in a temperature range from about 25° to about 55° C. for a period of about 2 to 3 hours. The quaternization reaction requires slightly higher temperatures and may be conducted from about 65° to about 95° C. for a period of about 1 to 8 hours. It is preferred, however, to conduct this reaction from about 80° to about 85° C. for about 2 to 3 hours.

If the quaternization reaction is performed first, the 2-chloro-2-hydroxyethylacetamid is added to the non-hydroxylic-pyridine solvent, and the reaction is conducted under the same conditions of temperature and stirring which are used for the quaternization reaction when it is performed as the second reaction. The acid halide is then added to the reaction mixture and the esterification reaction is conducted under the same conditions of temperature and stirring which are used for the esterification reaction when it is performed as the first reaction.

The isolation of the pyridinium salt from the solution produced by the process of the present invention, is not difficult. In one method of isolation, the reaction mixture is diluted with a suitable organic solvent, heated to a moderately elevated temperature in order to dissolve any precipitate which may be formed, and then cooled to precipitate the pyridinium chloride salt, which is recovered from the liquid by some suitable means such as filtration. The pyridinium salt, still wet with traces of the liquid from which it was precipitated, is then rinsed with a cold (0°–5° C.) lower alcohol. If a higher purity product is desired the pyridinium chloride is then dissolved in a recrystallization solvent and activated carbon and a filter aid are added to the solution. Upon removal of the activated carbon and filter aid from the solution, the solution is concentrated and cooled in order to precipitate the purified chloride salt which is then rinsed with a small portion of a warm aliphatic hydrocarbon solvent and dried. The process, including the above method of isolation, is illustrated on Flowsheet II.

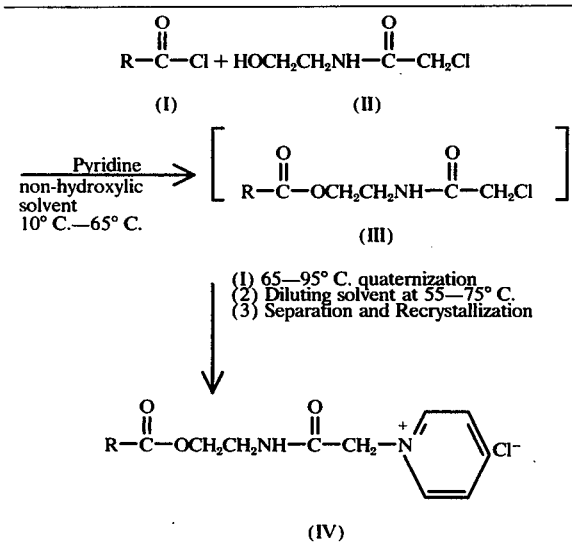

The solvents used to dilute the reaction mixture may include lower alcohols, such as methanol, ethanol, N-propanol, and isopropanol; ketones such as acetone and methyl ethyl ketone any hydrocarbons, such as benzene, toluene, xylene, hexane and heptane. The preferred diluting solvents are the lower alcohols, and the preferred alcohol is isopropanol. The final product may be recrystallized from a wide variety of organic solvents although the lower alcohols are preferred. The most desirable recrystallization solvent is methanol.

In the preferred isolation procedure, the reaction mixture is diluted with isopropanol; and the precipitate which forms upon the addition of the diluting solvent is then dissolved by warming the mixture to a temperature of from about 55° to about 75° C. The pyridinium chloride salt is then precipitated by cooling of the mixtures to a temperature of about 25° C. The precipitate is rinsed with isopropanol and the recrystallized from methanol. The recrystallization is conducted by dissolving the pyridinium chloride salt in non-boiling methanol, adding thereto a filter aid and activated carbon, removing said activated carbon and said filter aid, concentrating the methanol solution of the pyridinium salt to a volume of 30 to 40% of the original volume, and cooling the resulting solution to a temperature of −5° to about 15° C. in order to precipitate the pyridinium chloride salt. Finally, the pyridinium chloride salt is washed with a warm (35°–45° C.) aliphatic hydrocarbon solvent, (preferably hexane or heptane) and dried to yield the desired product.

The following examples are provided for illustrative purposes and may include particular features of the invention. However, the examples should not be construed as limiting the invention, many variations of which are possible without departing from the spirit or scope thereof. In the examples, all parts and percentages are by weight unless otherwise indicated.

EXAMPLE 1

To a suitable reaction vessel is added 689 grams (8.71 moles) of pyridine, 650 grams (88% real; 4.16 moles) of 2-chloro-N-2-hydroxythylacetamide and 540 grams of methyl ethyl ketone at room temperature. The reaction mixture is stirred while 1200 grams (98.6% real; 4.14 "apparent moles (1)") of molten stearoyl chloride is added continuously thereto over about 2 hours while allowing the reaction exotherm to increase the temperature to 47°–52° C. After the addition of the stearoyl chloride is completed the reaction mixture is heated to 80°–85° C. and stirred at 80°–85° C. for 3 hours. The reaction mixture is then cooled to 60°–65° C. and 2559 grams of isopropanol is added to the reaction mixture. The reaction mixture is then reheated to 60°–65° C. to dissolve all of the solids, cooled to 45°–50° C. and seeded with crystals of 1{ { [2-(stearoyloxy)ethyl] carbamoyl } methyl} pyridinium chloride to induce crystallization. After crystallization occurs, the reaction mixture is stirred at 45°–50° C. for 30 minutes and then cooled for 1½ hours at 30° C. The precipitate is filtered off, rinsed with cold (0°–5° C.) isopropanol and sucked partially dry.

The wet cake of crude product is dissolved in 11.24 liters of methanol and stirred with 50 grams of activated carbon and 50 grams of filter aid (Hyflo Super-Cel). The reaction mixture is clarified by filtration at 28° to about 30° C. and the clear filtrate is concentrated at about 25° to 35° C. under vacuum to remove 7.8 liters of the methanol. The solid is then rinsed with heptane (35°–45° C.) and dried to obtain 1137 g. of product (59% of theory) having the formula:

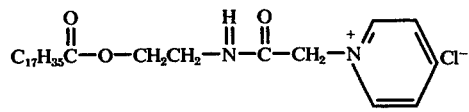

The white crystalline product has an assay of about 95.5% real and melts at 129.5° to 135.0° C. The pH of a 1% dispersion in water is 4.2.

Note: (1) Based on the apparent molecular weight of commercial stearic acid.

EXAMPLE 2

The following example illustrates the process of this invention to prepare crude product.

To a suitable reaction vessel equipped with a thermometer, stirrer, reflux condenser, dropping funnel and an inlet tube for nitrogen are added 443.7 grams (5.61 moles) of pyridine, 400.3 grams (94.1% real; 2.74 moles) of 2-chloro-N-2-hydroxyethylacetamide and 355 grams of methyl ethyl ketone at room temperature. The reaction mixture is stirred while 787.6 grams (98.6% real; 2.72 "apparent moles") of molten stearoyl chloride is added dropwise thereto over about four hours while allowing the reaction exotherm to increase the temperature to 45°–50° C. After the addition of the stearoyl chloride is completed, the reaction mixture temperature is increased to 55°–60° C. over a period of about 30 minutes. The reaction mixture is then heated to 80°–85° C. and maintained at 80°–85° C. for 4 hours.

The reflux condenser is then replaced by a condenser adapted for distillation and 230 ml. of methyl ethyl ketone is removed by distillation under reduced pressure (about 20–100 mm of mercury) at 84° C. over about 30 minutes. The reaction mixture is then flooded by adding 1356 grams of isopropanol thereto during which the temperature drops to about 55° C. The reaction mixture is then reheated to about 77°C. to dissolve all of the solids, and allowed to cool slowly to room temperature. After crystallization is completed the reaction mixture is warmed to about 30° C. and the precipitate is filtered off, rinsed twice with 350 ml. portions of cold (0°–5° C.) isopropanol, rinsed twice with 350 ml. portions of cold (0°–5° C.) acetone, sucked partially dry, and dried in a forced air oven at 80° C.

The white crystalline crude product obtained weighs 1013.3 grams (79.9% of theoretical), melts at 125.0° to 134.5° C., and assays for 94.0% real 1{ { [2-(stearoyloxy) ethyl]carbamoyl } methyl } pyridinium chloride. The pH of a 1% dispersion of this material in water is 4.2

What is claimed:

1. A method for producing a pyridinium salt represented by the formula:

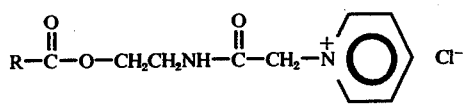

wherein R is an alkyl group containing from 11 to 17 carbon atoms, comprising combining approximately equimolar quantities of an aliphatic acid halide containing 12 to 18 carbon atoms and 2-chloro-N-2-hydroxyethylacetamide and slightly more than 2 moles of pyridine for each mole of 2-chloro-N-2-hydroxyethylacetamide present, in a non-hydroxylic organic solvent, stirring the mixture for a period of about 1 to 4 hours at a temperature of about 10° to 65° C., warming the mixture to a temperature of about 65° to 95° C. and stirring for about 1 to 8 hours, and isolating said pyridium salt.

2. A process according to claim 1 wherein said acid halide is selected from the group consisting of lauroyl chloride, myristoyl chloride, palmitoyl chloride, and stearoyl chloride.

3. A process according to claim 2 wherein said essentially non-hydroxylic solvent is methyl ethyl ketone.

4. A process according to claim 2 wherein said essentially non-hydroxylic solvent is di-n-butyl ether.

5. A process according to claim 3 wherein said acid halide is selected from the group consisting of lauroyl chloride and stearoyl chloride; and the mixture of 2-chloro-N-2-hydroxyethylacetamide, the acid halide, the non-hydroxylic organic solvent, and the pyridine are stirred for a period of about 2 to 3 hours at a temperature of about 25° to 55° C., and said mixture is then warmed to a temperature of about 80° to 85° C. and stirred for about 2 to 3 hours.

6. A method for producing a pyridinium salt represented by the formula:

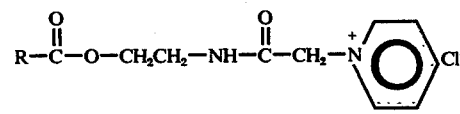

wherein R is an alkyl group containing from 11 to 17 carbon atoms, comprising combining 2-chloro-N-2-hydroxyethylacetamide with slightly more than 2 moles of pyridine for each mole of 2-chloro-N-2-hydroxyethylacetamide present, in a non-hydroxylic organic solvent, warming the mixture to a temperature of about 65° to 95° C. and stirring for about 1 to 8 hours, cooling the mixture to a temperature of about 10° to 65° C., adding thereto a number of moles of an aliphatic acid halide containing 12 to 18 carbon atoms approximately equal to the number of moles of 2-chloro-N-2-hydroxyethylacetamide originally present, stirring for about 1 to 4 hours and isolating said pyridinium salt.

7. A process according to claim 6 wherein said acid halide is selected from the group consisting of lauroyl chloride, myristoyl chloride, palmitoyl chloride, and stearoyl chloride.

8. A process according to claim 7 wherein said essentially non-hydroxylic solvent is methyl ethyl ketone.

9. A process according to claim 7 wherein said essentially non-hydroxylic solvent is di-n-butyl ether.

* * * * *